(12) United States Patent
Reinbigler et al.

(10) Patent No.: US 9,523,072 B2
(45) Date of Patent: Dec. 20, 2016

(54) METHOD FOR PROVIDING A CIRCUIT FOR BIOLOGICAL LIQUID AND CIRCUIT OBTAINED

(75) Inventors: Rene Reinbigler, Kirchheim (FR); Jean-Louis Weissenbach, Barr (FR)

(73) Assignee: EMD Millipore Corporation, Billerica, MA (US)

( * ) Notice: Subject to any disclaimer, the term of this patent is extended or adjusted under 35 U.S.C. 154(b) by 557 days.

(21) Appl. No.: 13/414,843

(22) Filed: Mar. 8, 2012

(65) Prior Publication Data

US 2012/0160356 A1    Jun. 28, 2012

Related U.S. Application Data

(62) Division of application No. 12/685,140, filed on Jan. 11, 2010.

(30) Foreign Application Priority Data

Jan. 23, 2009   (FR) ...................................... 09 50435

(51) Int. Cl.
*B29C 49/00* (2006.01)
*B01L 3/00* (2006.01)
(Continued)

(52) U.S. Cl.
CPC ............. *C12M 47/10* (2013.01); *A61L 2/0035* (2013.01); *B01L 3/502707* (2013.01); *B29C 33/02* (2013.01); *B29C 49/0047* (2013.01); *C12M 23/14* (2013.01); *C12M 23/26* (2013.01); *C12M 23/28* (2013.01); *C12M 29/04* (2013.01); *B01L 2200/0689* (2013.01); *B01L 2200/12* (2013.01); *B01L 2300/0816* (2013.01);
(Continued)

(58) Field of Classification Search
CPC .................. B29C 49/0047; B29C 2049/0057; B29C 2049/0063; B29C 33/02; B29C 65/02; B01L 3/502707; B01L 2200/0689; B01L 2300/0816; B01L 2400/0655; B01L 2200/12; B01L 2400/0487; B01L 2400/0481; Y10T 137/8593; Y10T 137/9029
See application file for complete search history.

(56) References Cited

U.S. PATENT DOCUMENTS 2,413,853 A    1/1947   Zademach et al.
2,787,403 A    4/1957   Carr et al.
(Continued)

FOREIGN PATENT DOCUMENTS

CN      101281204 A      10/2008
DE   10 2006 059459 A1    7/2008
(Continued)

OTHER PUBLICATIONS

Notice of Allowance mailed Mar. 18, 2014 in co-pending U.S. Appl. No. 13/116,508.
(Continued)

*Primary Examiner* — David C Mellon
(74) *Attorney, Agent, or Firm* — Nields, Lemack & Frame, LLC (57) ABSTRACT

A circuit for biological liquid including a bag having two films and a press. The press includes two shells that clamp the bag in a state in which pipes are formed between the films of the bag.

7 Claims, 7 Drawing Sheets

(51) Int. Cl.
  *B29L 31/00*     (2006.01)
  *C12M 1/00*     (2006.01)
  *B29C 33/02*    (2006.01)
  *A61L 2/00*     (2006.01)
  *B29C 65/02*    (2006.01)
  *B29K 23/00*    (2006.01)
  *B29L 9/00*     (2006.01)

(52) U.S. Cl.
  CPC . *B01L 2300/123* (2013.01); *B01L 2400/0481* (2013.01); *B01L 2400/0487* (2013.01); *B01L 2400/0655* (2013.01); *B29C 65/02* (2013.01); *B29C 2049/0057* (2013.01); *B29C 2049/0063* (2013.01); *B29K 2023/0616* (2013.01); *B29K 2023/083* (2013.01); *B29K 2023/086* (2013.01); *B29L 2009/00* (2013.01); *B29L 2031/7148* (2013.01); *Y10T 137/8593* (2015.04); *Y10T 137/9029* (2015.04)

(56) References Cited

U.S. PATENT DOCUMENTS

| | | | |
|---|---|---|---|
| 2,941,575 A * | 6/1960 | Malmberg et al. | 156/359 |
| 3,022,229 A | 2/1962 | Heden | |
| 3,179,117 A | 4/1965 | Gibson et al. | |
| 3,667,487 A | 6/1972 | Schoenbeck et al. | |
| 3,772,154 A | 11/1973 | Isenberg et al. | |
| 3,774,762 A | 11/1973 | Lichtenstein | |
| 4,113,623 A | 9/1978 | Koether et al. | |
| 4,332,750 A | 6/1982 | Roggenburg, Jr. et al. | |
| 4,370,983 A | 2/1983 | Lichtenstein | |
| 4,784,751 A | 11/1988 | McGehee | |
| 4,790,118 A | 12/1988 | Chilcoate | |
| 4,852,851 A | 8/1989 | Webster | |
| 4,855,236 A | 8/1989 | Levin | |
| 4,915,119 A | 4/1990 | Franklin | |
| 5,019,257 A | 5/1991 | Suzuki et al. | |
| 5,061,236 A | 10/1991 | Sutherland et al. | |
| 5,141,866 A | 8/1992 | Levin | |
| 5,265,912 A | 11/1993 | Natividad | |
| 5,290,518 A | 3/1994 | Johnson | |
| 5,324,422 A | 6/1994 | Colleran et al. | |
| 5,342,463 A | 8/1994 | Addeo et al. | |
| 5,520,885 A | 5/1996 | Coelho et al. | |
| 5,628,908 A | 5/1997 | Kamen et al. | |
| 5,645,723 A | 7/1997 | Fujishiro et al. | |
| 5,678,568 A | 10/1997 | Uchikubo et al. | |
| 5,711,916 A | 1/1998 | Riggs et al. | |
| 5,738,645 A | 4/1998 | Plotkin | |
| 5,985,653 A | 11/1999 | Armstrong et al. | |
| 6,073,942 A | 6/2000 | Heneveld, Sr. | |
| 6,099,734 A * | 8/2000 | Boggs et al. | 210/650 |
| 6,129,099 A | 10/2000 | Foster et al. | |
| 6,146,124 A | 11/2000 | Coelho et al. | |
| 6,186,998 B1 | 2/2001 | Inuzuka et al. | |
| 6,213,334 B1 | 4/2001 | Coelho et al. | |
| 6,228,255 B1 | 5/2001 | Peterson et al. | |
| 6,232,115 B1 | 5/2001 | Coelho et al. | |
| 6,303,025 B1 | 10/2001 | Houchens | |
| 6,361,642 B1 | 3/2002 | Bellamy et al. | |
| 6,670,169 B1 | 12/2003 | Schob et al. | |
| 6,808,675 B1 | 10/2004 | Coelho et al. | |
| 6,818,185 B1 | 11/2004 | Petersen et al. | |
| 6,902,706 B1 | 6/2005 | Colin et al. | |
| 6,982,063 B2 | 1/2006 | Hamel et al. | |
| 7,153,286 B2 | 12/2006 | Busby et al. | |
| 7,326,355 B2 | 2/2008 | Graetz et al. | |
| 7,458,560 B2 | 12/2008 | Muller | |
| 7,485,224 B2 | 2/2009 | Jones et al. | |
| 7,648,627 B2 | 1/2010 | Beden et al. | |
| 7,666,602 B2 | 2/2010 | Ammann et al. | |
| 7,867,189 B2 | 1/2011 | Childers et al. | |
| 7,935,074 B2 | 5/2011 | Plahey et al. | |
| 7,935,253 B2 | 5/2011 | Beulay et al. | |
| 8,114,276 B2 | 2/2012 | Childers et al. | |
| 8,163,172 B2 | 4/2012 | Beulay et al. | |
| 8,343,356 B2 | 1/2013 | Beulay et al. | |
| 8,383,397 B2 | 2/2013 | Wojciechowski et al. | |
| 8,499,794 B2 | 8/2013 | Takahashi et al. | |
| 8,505,959 B2 | 8/2013 | Darling, III | |
| 8,506,798 B2 | 8/2013 | Beulay et al. | |
| 8,557,113 B2 | 10/2013 | Beulay et al. | |
| 8,900,454 B2 | 12/2014 | Cirou et al. | |
| 8,906,229 B2 | 12/2014 | Cirou et al. | |
| 8,916,045 B2 | 12/2014 | Reinbigler et al. | |
| 8,921,096 B2 | 12/2014 | Weissenbach et al. | |
| 9,051,929 B2 | 6/2015 | Cirou et al. | |
| 9,174,145 B2 | 11/2015 | Weissenbach et al. | |
| 9,174,171 B2 | 11/2015 | Weissenbach et al. | |
| 9,181,941 B2 | 11/2015 | Cirou et al. | |
| 9,205,955 B2 | 12/2015 | Cirou et al. | |
| 9,259,687 B2 | 2/2016 | Weissenbach et al. | |
| 9,259,733 B2 | 2/2016 | Tuccelli et al. | |
| 2002/0147423 A1 | 10/2002 | Burbank et al. | |
| 2003/0040104 A1 | 2/2003 | Barbera-Guillem | |
| 2004/0031507 A1 | 2/2004 | Ross et al. | |
| 2004/0104153 A1 | 6/2004 | Yang | |
| 2004/0222341 A1 | 11/2004 | Breda et al. | |
| 2004/0259240 A1 | 12/2004 | Fadden | |
| 2005/0254879 A1 | 11/2005 | Gundersen et al. | |
| 2006/0024212 A1 | 2/2006 | Hwang | |
| 2006/0057030 A1 | 3/2006 | Lee et al. | |
| 2006/0118472 A1 | 6/2006 | Schick et al. | |
| 2006/0226333 A1 | 10/2006 | Newkirk | |
| 2007/0095364 A1 | 5/2007 | Watt | |
| 2007/0112297 A1 | 5/2007 | Plahey et al. | |
| 2007/0128087 A1 | 6/2007 | Cannizzaro et al. | |
| 2007/0199875 A1 | 8/2007 | Moorey et al. | |
| 2007/0278155 A1 | 12/2007 | Lo et al. | |
| 2008/0023045 A1 | 1/2008 | Miller et al. | |
| 2008/0057274 A1 | 3/2008 | Hagiwara et al. | |
| 2008/0213143 A1 | 9/2008 | Gyonouchi et al. | |
| 2008/0254962 A1 | 10/2008 | Mizuo et al. | |
| 2009/0011179 A1 | 1/2009 | Kikuchi et al. | |
| 2009/0042293 A1 | 2/2009 | Hata et al. | |
| 2009/0050756 A1 | 2/2009 | Newkirk et al. | |
| 2009/0101219 A1 | 4/2009 | Martini et al. | |
| 2009/0101552 A1 | 4/2009 | Fulkerson et al. | |
| 2009/0111179 A1 | 4/2009 | Hata et al. | |
| 2009/0180933 A1 | 7/2009 | Kauling et al. | |
| 2009/0215602 A1 | 8/2009 | Min et al. | |
| 2009/0294349 A1 | 12/2009 | Beulay et al. | |
| 2009/0314970 A1 | 12/2009 | McAvoy et al. | |
| 2010/0108920 A1 | 5/2010 | Tatarek | |
| 2010/0126927 A1 | 5/2010 | Blankenstein et al. | |
| 2010/0187167 A1 | 7/2010 | Reinbigler et al. | |
| 2010/0204765 A1 | 8/2010 | Hall et al. | |
| 2010/0206785 A1 | 8/2010 | Beulay et al. | |
| 2010/0234805 A1 | 9/2010 | Kaufmann et al. | |
| 2011/0174716 A1 | 7/2011 | Beulay et al. | |
| 2011/0297866 A1 | 12/2011 | Weber | |
| 2011/0303306 A1 | 12/2011 | Weber | |
| 2011/0315611 A1 | 12/2011 | Fulkerson et al. | |
| 2012/0006736 A1 | 1/2012 | Cirou et al. | |
| 2012/0018018 A1 | 1/2012 | Cirou et al. | |
| 2012/0031510 A1 | 2/2012 | Weissenbach et al. | |
| 2012/0053520 A1 | 3/2012 | Kirkpatrick | |
| 2012/0138173 A1 | 6/2012 | Cirou et al. | |
| 2012/0138522 A1 | 6/2012 | Cirou et al. | |
| 2012/0145616 A1 | 6/2012 | Weissenbach et al. | |
| 2012/0160342 A1 | 6/2012 | Weissenbach et al. | |
| 2012/0168390 A1 | 7/2012 | Beulay et al. | |
| 2012/0248025 A1 | 10/2012 | Reinbigler et al. | |
| 2012/0284991 A1 | 11/2012 | Kusz et al. | |
| 2013/0087490 A1 | 4/2013 | Beulay et al. | |
| 2013/0193073 A1 | 8/2013 | Hogard et al. | |
| 2013/0210130 A1 | 8/2013 | Larcher et al. | |
| 2013/0236130 A1 | 9/2013 | Cirou et al. | |
| 2013/0240065 A1 | 9/2013 | Weissenbach et al. | |
| 2013/0292319 A1 | 11/2013 | Fulkerson et al. | |
| 2014/0069537 A1 | 3/2014 | Cirou et al. | |
| 2014/0263062 A1 | 9/2014 | Updyke et al. | |
| 2015/0008184 A1 | 1/2015 | Cirou et al. | |

(56) References Cited

U.S. PATENT DOCUMENTS

| | | | |
|---|---|---|---|
| 2015/0013773 A1 | 1/2015 | Cirou et al. | |
| 2015/0083320 A1 | 3/2015 | Putnam | |
| 2015/0190809 A1 | 7/2015 | Tuccelli et al. | |
| 2015/0204450 A1 | 7/2015 | Tuccelli et al. | |

FOREIGN PATENT DOCUMENTS

| | | | |
|---|---|---|---|
| DE | 10 2008 003823 A1 | 7/2008 | |
| EP | 0479047 A2 | 4/1992 | |
| EP | 0803723 A1 | 10/1997 | |
| EP | 1195171 A2 | 4/2002 | |
| EP | 1239277 A1 | 9/2002 | |
| EP | 2044964 A2 | 4/2009 | |
| EP | 2130903 A1 | 12/2009 | |
| EP | 2208534 A1 | 7/2010 | |
| EP | 2210666 A1 | 7/2010 | |
| EP | 2228635 A1 | 9/2010 | |
| FR | 2241615 A1 | 3/1975 | |
| FR | 2673853 A1 | 9/1992 | |
| FR | 2931838 A1 | 12/2009 | |
| FR | 2940145 A1 | 6/2010 | |
| FR | 2955119 A1 | 7/2011 | |
| FR | 2960796 A1 | 12/2011 | |
| FR | 2961711 A1 | 12/2011 | |
| GB | 1434786 | 5/1976 | |
| GB | 2448858 A | 11/2008 | |
| JP | 62-081543 A | 4/1987 | |
| JP | 2010-502405 A | 1/2010 | |
| WO | 93/03295 A1 | 2/1993 | |
| WO | 04/05346 A1 | 3/1994 | |
| WO | 00/48703 A1 | 8/2000 | |
| WO | 2005/090403 A2 | 9/2005 | |
| WO | 2006/043895 A1 | 4/2006 | |
| WO | 2007/094254 A1 | 8/2007 | |
| WO | 2008/033788 A2 | 3/2008 | |
| WO | 2008/064242 A2 | 5/2008 | |
| WO | 2008/071351 A1 | 6/2008 | |
| WO | 2008/120021 A1 | 10/2008 | |
| WO | 2009/017614 A1 | 2/2009 | |
| WO | 2009/073567 A1 | 6/2009 | |
| WO | 2009/157852 A1 | 12/2009 | |
| WO | 2010/084432 A1 | 7/2010 | |
| WO | 2010/094249 A1 | 8/2010 | |
| WO | 2011/161609 A1 | 12/2011 | |

OTHER PUBLICATIONS

Final Rejection mailed Mar. 26, 2014 in co-pending U.S. Appl. No. 13/187,698.
Notice of Allowance mailed Apr. 1, 2014 in co-pending U.S. Appl. No. 13/153,809.
Office Action mailed Aug. 25, 2014 in co-pending U.S. Appl. No. 13/004,425.
Office Action mailed Jul. 30, 2014 in co-pending U.S. Appl. No. 14/080,826.
Notice of Allowance mailed Aug. 11, 2014 in co-pending U.S. Appl. No. 13/116,508.
Office Action mailed Jul. 24, 2014 in co-pending U.S. Appl. No. 13/187,698.
Notice of Allowance mailed Aug. 8, 2014 in co-pending U.S. Appl. No. 13/153,809.
Notice of Allowance mailed Jul. 2, 2014 in co-pending U.S. Appl. No. 13/430,734.
Notice of Allowance mailed Aug. 12, 2014 in co-pending U.S. Appl. No. 13/430,734.
Korean communication, with English translation, dated Jul. 31, 2014 in co-pending Korean patent application No. 10-2013-7000355.
Korean communication, with English translation, dated Jul. 31, 2014 in co-pending Korean patent application No. KR 10-2013-7001692 .
Korean communication, with English translation, dated Jul. 31, 2014 in co-pending Korean patent application No. KR 10-2013-7000366.
Korean communication, with English translation, dated Jul. 31, 2014 in co-pending Korean patent application No. KR 10-2013-7000356.
Notice of Allowance mailed Jun. 18, 2013 in U.S. Appl. No. 13/688,255, now U.S. Pat. No. 8,506,798.
Office Action—Restriction—mailed Oct. 15, 2013 in co-pending U.S. Appl. No. 13/004,425.
Office Action mailed Oct. 9, 2013 in co-pending U.S. Appl. No. 13/116,508.
Office Action mailed Oct. 18, 2013 in co-pending U.S. Appl. No. 13/116,508.
Notice of Allowance mailed Sep. 6, 2013 in co-pending U.S. Appl. No. 12/592,901, now U.S. Pat. No. 8,557,113.
Office Action mailed Oct. 23, 2013 in co-pending U.S. Appl. No. 13/153,809.
Written Opinion of the International Searching Authority mailed Jun. 8, 2011 in co-pending PCT application No. PCT/IB2011/050089.
International Preliminary Report on Patentability mailed Jul. 26, 2012 in co-pending PCT application No. PCT/IB2011/050089.
International Preliminary Report on Patentability mailed Dec. 20, 2012 in co-pending PCT application No. PCT/IB2011/052447.
Written Opinion of the International Searching Authority mailed Sep. 29, 2011 in co-pending PCT application No. PCT/IB2011/052676.
International Preliminary Report on Patentability mailed Jan. 10, 2013 in co-pending PCT application No. PCT/IB2011/052676.
Written Opinion of the International Searching Authority mailed Aug. 29, 2011 in co-pending PCT application No. PCT/IB2011/052679.
International Preliminary Report on Patentability mailed Jan. 10, 2013 in co-pending PCT application No. PCT/IB2011/052679.
Written Opinion of the International Searching Authority mailed Aug. 2, 2011 in co-pending PCT application No. PCT/IB2011/052448.
International Preliminary Report on Patentability mailed Dec. 20, 2012 in co-pending PCT application No. PCT/IB2011/052448.
International Preliminary Report on Patentability mailed Dec. 20, 2012 in co-pending PCT application No. PCT/IB2011/052450.
International Search Report mailed Sep. 4, 2012 in co-pending PCT application No. PCT/IB2012/051424.
Office Action—Restriction—mailed Apr. 25, 2013 in co-pending U.S. Appl. No. 13/161,975.
Notice of Allowance mailed May 13, 2013 in co-pending U.S. Appl. No. 13/161,975.
Office Action mailed May 9, 2013 in co-pending U.S. Appl. No. 12/592,901.
Notice of Allowance mailed May 6, 2013 in co-pending U.S. Appl. No. 13/153,804.
Office Action mailed Jun. 28, 2012 in corresponding U.S. Appl. No. 12/685,140.
Chinese Communication, with English translation, dated Sep. 27, 2012 in corresponding Chinese patent application No. CN 201010004496.1.
Final Rejection mailed Jan. 24, 2013 in corresponding U.S. Appl. No. 12/685,140.
Office Action mailed Feb. 22, 2013 in co-pending U.S. Appl. No. 13/688,255.
Notice of Allowance mailed Apr. 1, 2013 in co-pending U.S. Appl. No. 13/161,983.
Office Action—Restriction—mailed Apr. 2, 2013 in co-pending U.S. Appl. No. 13/153,804.
Extended European Search Report and Search Opinion received for corresponding EP Patent Application No. 10290005.7, mailed on May 17, 2010, 5 pages.
International Preliminary Report on Patentability received for corresponding PCT application No. PCT/IB2010/050102, mailed on Aug. 4, 2011, 8 pages.

(56) References Cited

OTHER PUBLICATIONS

International Search Report and Written Opinion received for corresponding PCT application No. PCT/IB2010/050102, mailed on May 7, 2010, 10 pages.
French Search Report dated Oct. 16, 2009 in corresponding French Patent Application No. FR 0950435.
Office Action—Restriction—mailed Jan. 27, 2012 in corresponding U.S. Appl. No. 12/685,140.
Notice of Allowance mailed Apr. 14, 2014 in co-pending U.S. Appl. No. 13/116,508.
Notice of Allowance mailed Apr. 14, 2014 in co-pending U.S. Appl. No. 13/153,809.
Final Rejection mailed Jun. 23, 2014 in corresponding U.S. Appl. No. 12/685,140.
Notice of Allowance mailed Sep. 3, 2014 in co-pending U.S. Appl. No. 13/116,508.
Notice of Allowance mailed Sep. 2, 2014 in co-pending U.S. Appl. No. 13/153,809.
Notice of Allowance mailed Sep. 29, 2014 in co-pending U.S. Appl. No. 13/430,734.
Notice of Allowance mailed Nov. 6, 2014 in co-pending U.S. Appl. No. 13/187,698.
French Search Report dated Feb. 9, 2009 in co-pending foreign patent application No. FR 0853629.
French Search Report dated Sep. 24, 2010 in co-pending foreign patent application No. FR 1050209.
French Search Report dated Nov. 25, 2010 in co-pending foreign patent application No. FR 1054514.
French Search Report dated Nov. 12, 2010 in co-pending foreign patent application No. FR 1055025.
French Search Report dated Feb. 3, 2011 in co-pending foreign patent application No. FR 1055026.
French Search Report dated May 24, 2011 in co-pending foreign patent application No. FR 1056421.
Extended European Search Report for co-pending foreign patent application No. EP 09290938.1, mailed Apr. 6, 2010, 5 pages.
French Search Report dated Nov. 22, 2010 in co-pending foreign patent application No. FR 1054517.
French Search Report dated Nov. 22, 2010 in co-pending foreign patent application No. FR 1054516.
French Search Report dated Nov. 17, 2011 in corresponding foreign patent application No. FR 1152556.
Office Action mailed Jun. 11, 2012 in co-pending U.S. Appl. No. 13/420,906.
Office Action mailed Jun. 5, 2012 in co-pending U.S. Appl. No. 12/592,901.
International Search Report/Written Opinion mailed Sep. 30, 2011 in co-pending PCT Application No. PCT/IB2011/052447.
International Search Report/Written Opinion mailed Sep. 28, 2011 in co-pending PCT Application No. PCT/IB2011/052450.
International Search Report mailed Jun. 8, 2011 in co-pending PCT Application No. PCT/IB2011/050089.
International Search Report mailed Sep. 29, 2011 in co-pending PCT Application No. PCT/IB2011/052676.
International Search Report mailed Aug. 29, 2011 in co-pending PCT Application No. PCT/IB2011/052679.
International Search Report mailed Aug. 2, 2011 in co-pending PCT Application No. PCT/IB2011/052448.
Notice of Allowance mailed Feb. 18, 2014 in co-pending U.S. Appl. No. 13/116,508.
Notice of Allowance mailed Feb. 3, 2014 in co-pending U.S. Appl. No. 13/430,734.
Notice of Allowance mailed Oct. 17, 2012 in U.S. Appl. No. 13/420,906, now U.S. Pat. No. 8,343,356.
Office Action mailed Oct. 25, 2013 in co-pending U.S. Appl. No. 13/187,698.
Office Action mailed Dec. 17, 2013 in corresponding U.S. Appl. No. 12/685,140.
Office Action mailed Jan. 16, 2014 in co-pending U.S. Appl. No. 13/004,425.
Notice of Allowance mailed Jul. 2, 2015 in co-pending U.S. Appl. No. 13/161,698.
Notice of Allowance mailed Jul. 2, 2015 in co-pending U.S. Appl. No. 13/153,804.
Office Action mailed Jan. 6, 2015 in corresponding U.S. Appl. No. 12/685,140.
Notice of Allowance mailed Feb. 2, 2015 in co-pending U.S. Appl. No. 13/004,425.
Final Rejection mailed Mar. 11, 2015 in co-pending U.S. Appl. No. 14/080,826.
Notice of Allowance mailed Nov. 13, 2015 in co-pending U.S. Appl. No. 13/889,616.
Final Rejection mailed Aug. 19, 2015 in co-pending U.S. Appl. No. 12/685,140.
Notice of Allowance mailed Jul. 13, 2015 in co-pending U.S. Appl, No. 14/080,826.
Notice of Allowance mailed Jul. 28, 2015 in co-pending U.S. Appl. No. 14/080,826.
Notice of Allowance mailed Jul. 20, 2015 in co-pending U.S. Appl. No. 13/161,975.
Notice of Allowance mailed Apr. 6, 2016 in co-pending U.S. Appl. No. 12/685,140
Office action mailed Mar. 9, 2016 in co-pending U.S. Appl. No. 13/872,248.
Final rejection mailed Jun. 16, 2016 in co-pending U.S. Appl. No. 13/872,248.
Millipore, "Process Containers," published at <http://www.millipore.com/bioproduction/bp3/containers>, available on Apr. 5, 2008, 2 pages.
International Search Report and Written Opinion mailed Nov. 8, 2013 in co-pending PCT application No. PCT/IB2013/055926 (P-12/184-PCT).
International Preliminary Report on Patentability issued Feb. 5, 2015 in co-pending PCT application no. PCT/IB2013/055926 (P-121184-PCT).
International Search Report and Written Opinion mailed Dec. 5, 2013 in co-pending PCT application No. PCT/IB2013/055925 (P-121186-PCT).
International Preliminary Report on Patentability issued Feb. 5, 2015 in co-pending PCT application No. PCT/IB2013/055925 (P-12/186-PCT).
Notice of Allowance mailed Jul. 1, 2016 in co-pending U.S. Appl. No. 12/685,140.
Office action mailed Jun. 20, 2016 in co-pending U.S. Appl. No. 14/413,556 (P-12/186)
Notice of Allowance mailed Sep. 30, 2016 in co-pending U.S. Appl. No. 12/685,140.
Office action mailed Nov. 2, 2016 in-pending U.S. Appl. No. 13/872,248.
Final rejection mailed Oct. 25, 2016 in co-pending U.S. Appl. No. 14/413,556 (P-12/186).

* cited by examiner

METHOD FOR PROVIDING A CIRCUIT FOR BIOLOGICAL LIQUID AND CIRCUIT OBTAINED

This application is a divisional of U.S. patent application Ser. No. 12/685,140 filed Jan. 11, 2010, the disclosure of which is incorporated herein by reference.

PRIORITY CLAIMED

French patent application No. 0950435 filed on Jan. 23, 2009

The invention relates to circuits for biological liquid, in particular, but not exclusively, for purifying a biopharmaceutical liquid in order to obtain a product such as monoclonal antibodies, vaccines or recombinant proteins.

It is known that biopharmaceutical liquids are in general obtained by culture in a bioreactor and that they must then be treated to achieve the required characteristics of purity, concentration, absence of viruses, etc.

These treatments are conventionally carried out in dedicated installations, with stainless steel pipes and other components such as tanks and filter housings, which necessitate operations before and after the actual treatment, which are relatively onerous, in particular operations of cleaning after use.

Within the last few years, these treatments have alternatively been carried out in installations in which the components in contact with the liquid are single-use components.

Such single-use components have the advantage of avoiding cleaning operations, but, to provide the required degree of security, the implementation of an installation with such components necessitates operations of selection, assembly and verification which are relatively complex.

This is especially the case when the number of pipes and other circuit components (connectors, valves, etc.) is high and/or when the operating pressure is high.

According to a first aspect, the invention aims to provide a circuit for biological liquid that is particularly simple, convenient and reliable.

To that end, it provides a method for providing a circuit for biological liquid comprising a plurality of connectors and a network for routing liquid between said connectors, characterized in that it comprises:
  the step of obtaining a bag comprising two flexible films attached together by a seal delimiting a closed contour with, open on the inside and on the outside of said contour, said routing network connectors and an inflating connector;
  the step of obtaining a press comprising two shells adapted to cooperate with said bag to form, between said films, by clamping said bag between said shells and by injecting an inflating agent via said inflating connector, pipes of said routing network; said bag and said press being selected in order for at least one said pipe to have a contour of which at least one portion is delimited exclusively by cooperation with said press; and
  the step of forming said pipes by clamping said bag between said shells and by injecting an inflating agent via said inflating connector.

In the circuit provided by the method according to the invention, the pipes of the fluid routing network are not pre-formed, or in any event not totally pre-formed, at the initial state of the bag that is used. On the contrary, at least one pipe has a contour of which at least one portion is exclusively delimited by cooperation with the press.

On the bag used, in the initial state, the routing network connectors open into the same space, within the bag, surrounded by the seal with a closed contour.

Due to the fact that the inflating connector opens into the same space, the injection of the inflating agent by that connector enables inflation of that space, provided that this agent cannot escape by the other connectors.

By virtue of this inflation, the films can press against the faces of the shells with which they are in contact, including the parts of those faces which are recessed (the parts which serve for the shaping of the pipes).

The clamping of the bag between the shells enables the contact zones between the films bordering the pipes formed to be made fluid-tight.

As explained later, the inflation may be carried out before the clamping of the bag, after the clamping of the bag, or partially before and partially after the clamping of the bag.

Once the step of clamping the bag between the shells and of injecting an inflating agent by the inflating connector has been carried out, the circuit is ready to be placed in service.

This may for example be performed by removing the plugs obturating the routing network connectors (if such plugs were used to enable the inflation of the pipes with the inflating agent) and by connecting those connectors to different containers for liquid, such as a source container of liquid to treat and a collecting container for treated liquid. The connections with the containers are made by simple tubing and/or by sections of more complex circuit comprising for example a pump.

Of course, in use, the bag remains clamped between the shells.

In the method according to the invention there is no step of providing conventional tube sets and connectors which must be preassembled.

The circuit obtained by the method according to the invention at the same time provides the integral character conferred by shaping it from a bag, the disposable character of a bag and the character of stiffness and strength of the shells.

Furthermore, the fact of shaping the pipes of the circuit with the shells which clamp the bag when the circuit is in use, provides, relative to the solution of shaping the pipes beforehand in a separate manufacturing mold, the advantage of simplifying the manufacturing of the bag and the advantage of eliminating the risks from undesirable stresses in the films of the bag when the circuit is in use, which stresses could have existed due to the differences in shaping, linked to the manufacturing tolerances, between the manufacturing mold and the shells of the press for the circuit.

According to preferred features of the method according to the invention:
  said inflating connector is separate from said routing network connectors;
  said inflating agent is pneumatic;
  said step of forming said pipes comprises the step of injecting an inflating agent before the step of clamping said bag between said shells; and/or
  said step of injecting an inflating agent is preceded by a step of pre-closing said press in which said bag is in immediate proximity to each of the two shells.

According to a second aspect, the invention also concerns the circuit obtained by the method set forth above.

To that end it provides a circuit for biological liquid which is capable of being obtained by the method as described above, comprising a plurality of connectors and a network for routing liquid between said connectors, characterized in that this it comprises:

a bag comprising two flexible films attached together by a seal delimiting a closed contour with, open on the inside and on the outside of said contour, said routing network connectors and an inflating connector; and a press comprising two shells clamping said bag in a state in which are formed, between said films, pipes of said network for routing liquid, inflated by an inflating agent, at least one said pipe having a contour of which at least one portion is delimited exclusively by cooperation with said press.

According to preferred features:

each said shell comprises a shaping channel for each said pipe;

each said shaping channel is of semi-circular cross-section;

at least one said shell comprises a shaping channel for each said pipe, with each said shaping channel being bordered on each side by a groove in which is accommodated a respective bead of a network of beads serving to apply said films against each other along said pipes;

at least one said shell comprises means for welding said films along said pipes;

the circuit comprises at least one filter enclosed in said bag;

at least one said shell comprises at least one actuator of a pinch valve of a said pipe; and/or at least one said shell comprises at least one sensor of a physico-chemical value.

The disclosure of the invention will now be continued with the detailed description of embodiments, given below by way of illustrative and non-limiting example, with reference to the accompanying drawings, in which.

Figure 1:
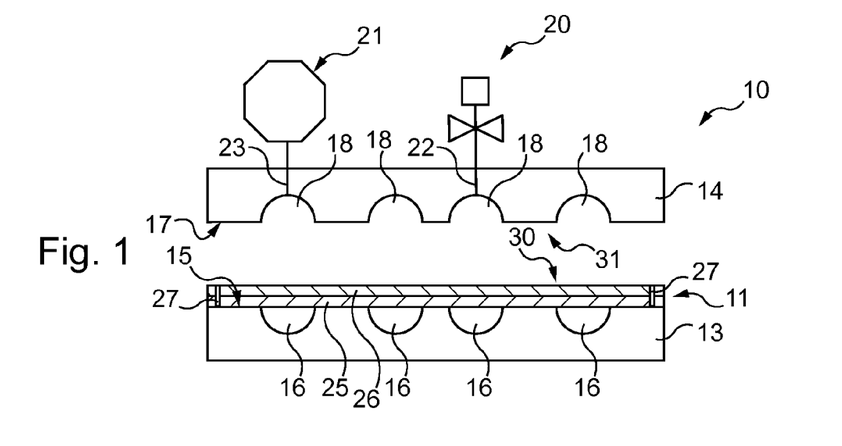
FIG. 1 is a diagram of a first embodiment of a press and a of bag enabling a circuit in accordance with the invention to be obtained, the bag resting on the lower shell of the press.
Figure 2:
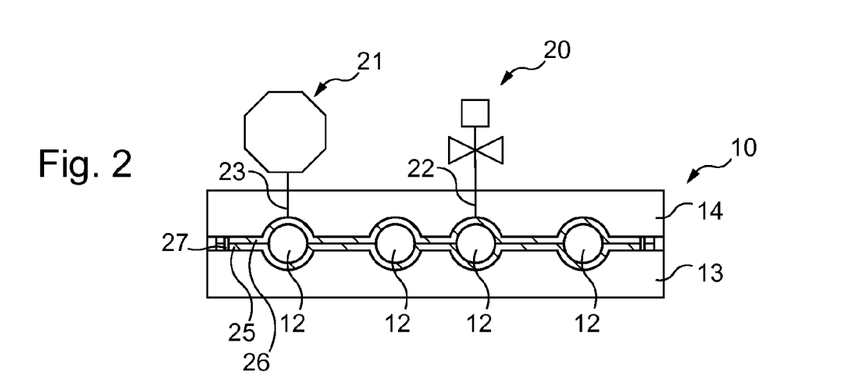
FIG. 2 is a similar diagram to FIG. 1, but in which the shells of the press clamp the bag, in a state in which the circuit is ready to be placed in service.
Figure 5:
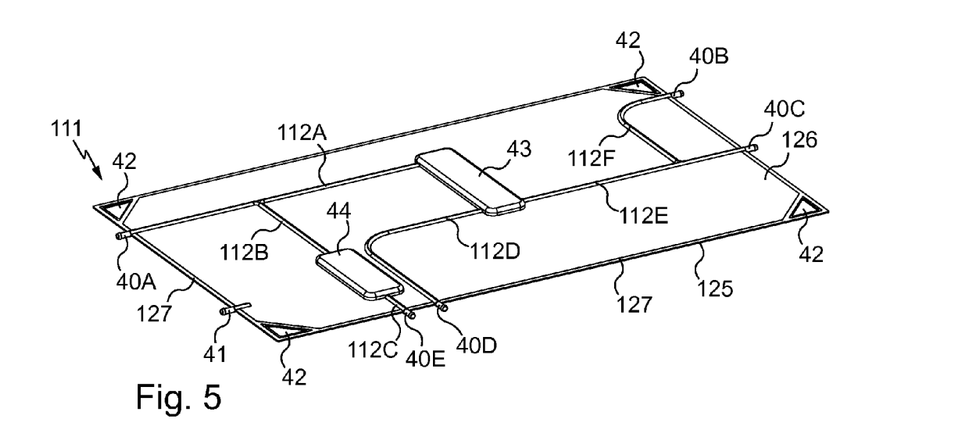
FIG. 5 is a perspective view of the bag of that circuit, in its state when the circuit is ready to be placed in service.

The press 10 and the bag 11 illustrated in FIGS. 1 and 2 make it possible to obtain a circuit for processing a biological liquid comprising a plurality of connectors for liquid (which connectors are not illustrated but are similar to the connectors 40A to 40E of the bag 111 of FIG. 5) and a network for routing liquid between those connectors. Some of the pipes 12 of that network can be seen in FIG. 2.

The press 10 comprises two shells 13 and 14.

The shells 13 and 14 are each formed from a sold block of stiff material. Here, the shells 13 and 14 are of stainless steel and are each of generally parallelepiped shape.

Shell 13 has a reference surface 15, which is planar here, and a plurality of channels 16 recessed into surface 15.

In the same way, shell 14 has a reference surface 17 which is planar here and channels 18 recessed relative to surface 17, with surfaces 15 and 17 being of similar dimensions and the arrangement of the channels 18 being the mirror image of the arrangement of the channels 16.

Channels 16 and 18 are of semi-circular cross-section.

The surfaces 15 and 17 may thus be applied against each other with the channels 16 and 18 in register with each other to delimit a network of cavities which are each generally tubular.

In addition to the shells 13 and 14, the press 10 comprises, here implanted on shell 14, actuators 20 of pinch valves and sensors 21 of a physico-chemical value, for example pressure or temperature.

The actuators 20 each comprise a body 22 attached to shell 14 and a moveable finger able to adopt a working position and a retracted position. In the working position, the moveable finger projects from one of the channels 18.

Each sensor 21 comprises a body 23 attached to shell 14 in register with a channel 18, with the distal end of the body 23 opening into that channel 18.

Bag 11 comprises two flexible films 25 and 26 attached to each other by a seal 27 delimiting a closed contour.

Here, each of the films 25 and 26 is a PureFlex™ film from the applicant. This is a co-extruded film comprising four layers, respectively, from the inside to the outside, a layer of ultra low density polyethylene (ULDPE) forming the material for contact with the liquid, a copolymer of ethylene and vinyl alcohol (EVOH) forming a barrier to gases, a copolymer layer of ethylene and vinyl acetate (EVA) and a layer of ultra low density polyethylene (ULDPE) forming the outer layers.

The seal 27 is a weld bead formed at the periphery of the films 25 and 26.

In addition to films 25 and 26 and connectors for liquid, bag 11 comprises a connector for a pneumatic agent (not illustrated, but similar to connector 41 of bag 111 in FIG. 5).

The dimensions of bag 11 correspond to those of the reference surfaces 15 and 17 of the shells 13 and 14.

Bag 11 is intended to be clamped by shells 13 and 14 with one of the faces of bag 11 in contact with the face 30 of shell 13 (this face having surface 15 and channels 16), and with the other face of bag 11 being in contact with face 31 of shell 14 (this face having surface 17 and channels 18).

FIG. 1 shows bag 11 in place between shells 13 and 14, here with bag 11 resting on face 30 and shell 14 away from bag 11.

Shell 14 is then brought towards shell 13, until surface 17 is in contact or practically in contact with bag 11, but without shells 13 and 14 being pressed against each other (pre-closing position).

Bag 11 is then inflated: the connectors for liquid are obturated and a pneumatic agent is injected by the connector provided for that purpose.

The effect of inflating bag 11 is that films 25 and 26 respectively conforms to face 30 of shell 13 and face 31 of shell 14.

The press 10 is then closed, that is to say that shells 13 and 14 are strongly pressed against each other while sandwiching the bag 11 (closed position in which bag 11 is clamped between shells 13 and 14).

Films 25 and 26 are then pressed against faces 30 and 31, including at channels 16 and 18 where they form the pipes 12, as shown in FIG. 2.

The press 10 and the bag 11 then form a circuit for treating a biological liquid which is ready to be placed in service.

Each actuator 20 enables a pipe 12 to be pinched between its moveable finger and shell 13, to allow or prevent the passage of the liquid at that location.

The sensors 21 have their distal end (the sensitive end) in contact with a pipe 12. Each sensor 21 makes it possible to know a physico-chemical characteristic of the liquid flowing in pipe 12 with which its distal end is in contact, for example its temperature or its pressure without having to actually touch the fluid. Such sensors are well known and include for example pressure sensors that measure pressure via the outer surface of the bag.

When the biological liquid to process in the circuit formed by press 10 and bag 11 has to be protected from contaminations, bag 11 is provided with obturating plugs in place on each of the connectors for liquid and on the connector for a pneumatic agent and it is sterilized, for example by gamma irradiation. The pneumatic agent injected inside bag 11 is purified. For instance, the pneumatic agent is compressed air purified through an hydrophobic filter such as an AERVENT® available from the company Millipore connected to the inflation connector.

Figure 3:
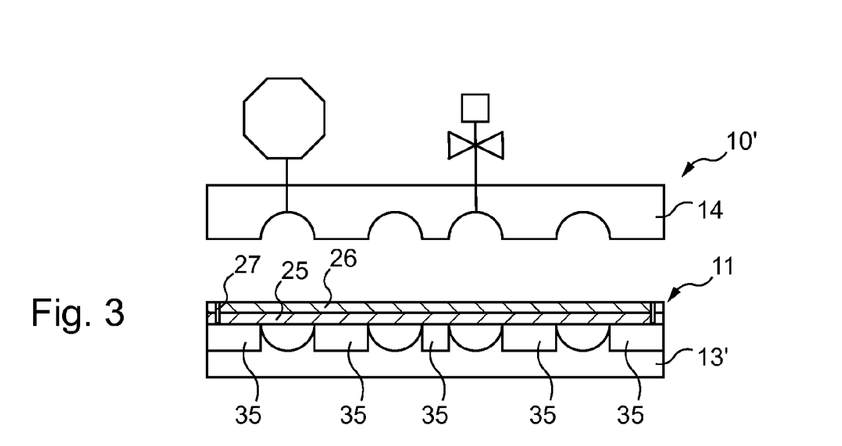
FIG. 3 is a similar view to FIG. 1, for a variant of the first embodiment of the press in which resistors are provided for welding the two films of the bag.

FIG. 3 shows a variant 10' of press 10, in which shell 13 is replaced by a shell 13' identical to shell 13 apart from it comprising a heating device 35 such as an electrical resistor, to weld the films 25 and 26 on respective opposite sides of the pipes 12 in order to make the delimitation of the pipes 12 permanent. Of course, the welding is carried out in closed position of the press.

With the aid of FIGS. 4 to 9 a description will now be given of a second embodiment of a press and of a bag to obtain a circuit in accordance with the invention.

For similar parts the same numerical references have been kept as on FIGS. 1 and 2, to which 100 has been added.

Whereas in press 10 or 10' (FIGS. 1 to 3), the actuators 20 and the sensors 21 are implanted on the same shell, in press 110 of the embodiment of FIGS. 4 to 9, the actuators 120A to 120G are implanted on one of the shells (here shell 114) and the sensors 121A to 121D on the other shell (here shell 113).

As can be seen more particularly in FIG. 5, bag 111 comprises five connectors 40A to 40E for liquid and one connector 41 for a pneumatic agent.

In the initial state of bag 111, none of the pipes 112A to 112F has been formed. The connectors 40A to 40E then each appear as connector 41, which is the only one not to be associated with a liquid routing network pipe at the time of the shaping of bag 111 by the press 110.

Films 125 and 126 which form bag 111 are each rectangular and of the same dimensions. They are attached to each other by a peripheral seal 127, here a weld in the form of a weld bead extending parallel to the edge of the films, except in the corners where the internal limit of the weld is oblique. In each corner, an opening 42 is formed, here with a right-angle triangle contour, which is surrounded by the weld 127.

It will be noted that the connectors for liquid 40A to 40E and the connector 41 for a pneumatic agent all open on the inside and on the outside of the closed contour delimited by the weld 127.

Within the contour delimited by weld 127, bag 111 encloses two filters 43 and 44 disposed between the films 125 and 126 at predetermined locations, each of the filters 43 and 44 being attached to those films, here by welding.

In the initial state of bag 111, filters 43 and 44 comprise, at each of the locations where they are to be connected to a pipe for liquid, a end piece for interfacing with that pipe.

Figure 4:
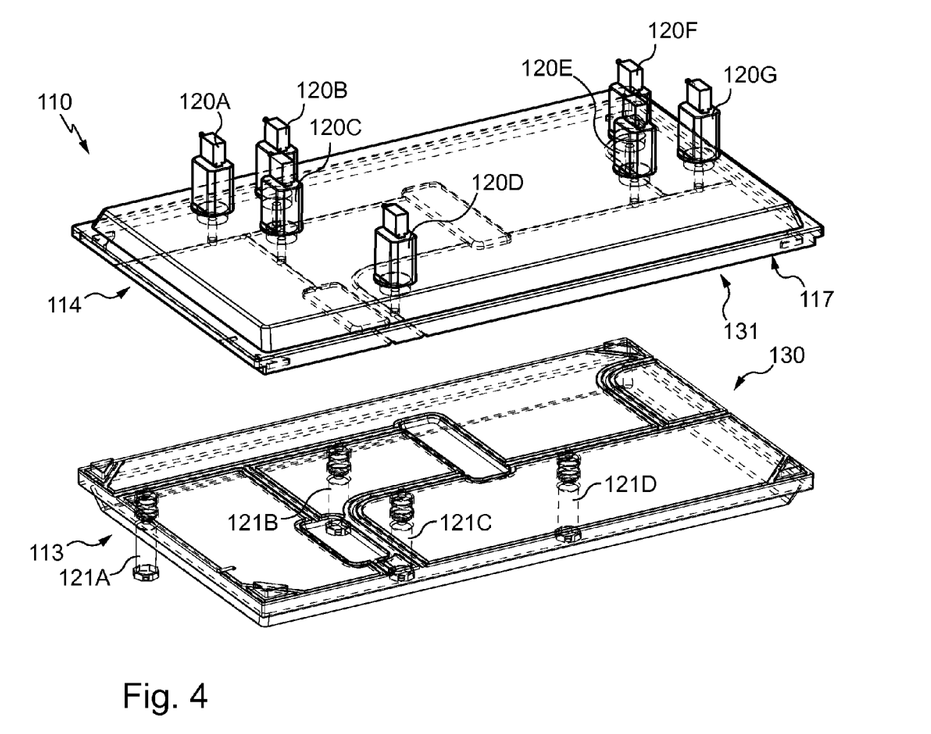
FIG. 4 is a relatively detailed perspective view of the shells of a second embodiment of a press enabling a circuit in accordance with the invention to be implemented.
Figure 7:
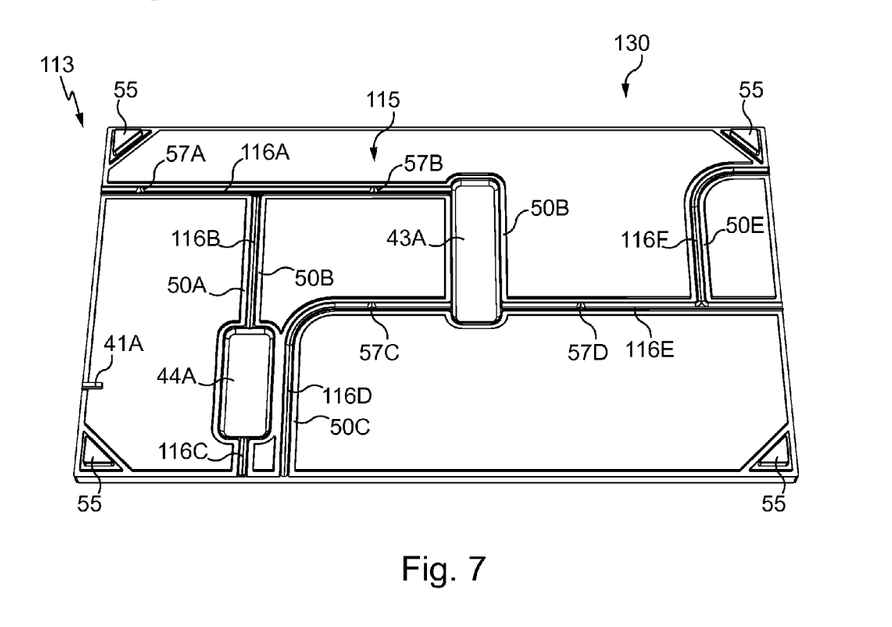
FIG. 7 is a perspective view of the lower shell of FIG. 4, showing its face intended to be in contact with the bag.
Figure 9:
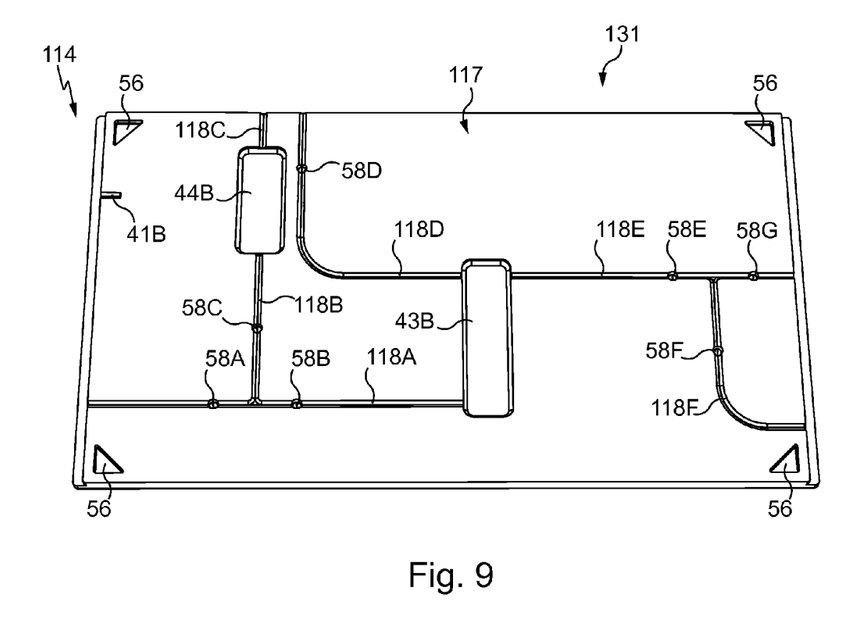
FIG. 9 is a perspective view of the upper shell of FIG. 4, showing its face intended to be in contact with the bag.
Figure 10:
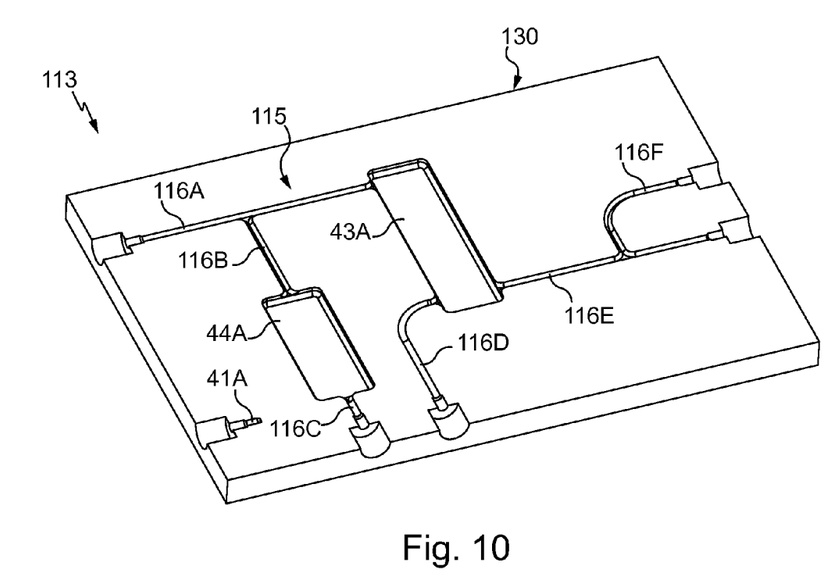
FIGS. 10 and 11 are respectively a perspective view and a plan view of a variant of the lower shell shown in FIGS. 4 and 7, in which only the recesses for implementing the network for routing liquid and for accommodating the connectors of the bag are represented (to simplify, the other details such as the apertures for the valves and the sensors or such as the positioning bosses and cavities are not illustrated)
Figure 11:
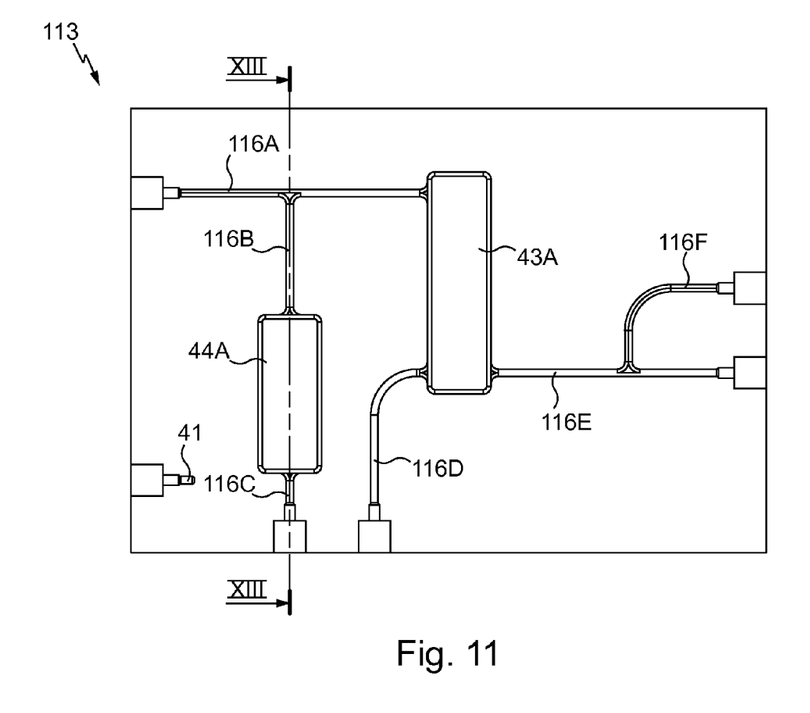
Figure 12:
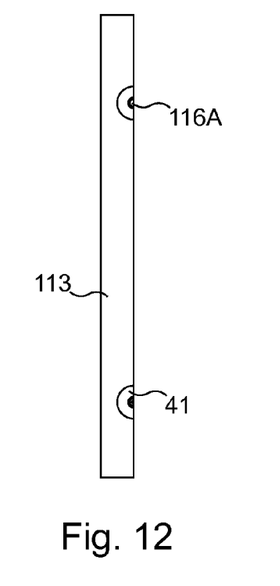
FIG. 12 is an elevation view from the side which can be seen on the left in FIG. 11.
Figure 13:
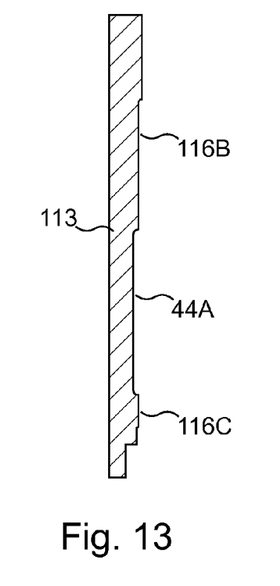
FIG. 13 is the section view on XIII-XIII of FIG. 11.
Figure 14:
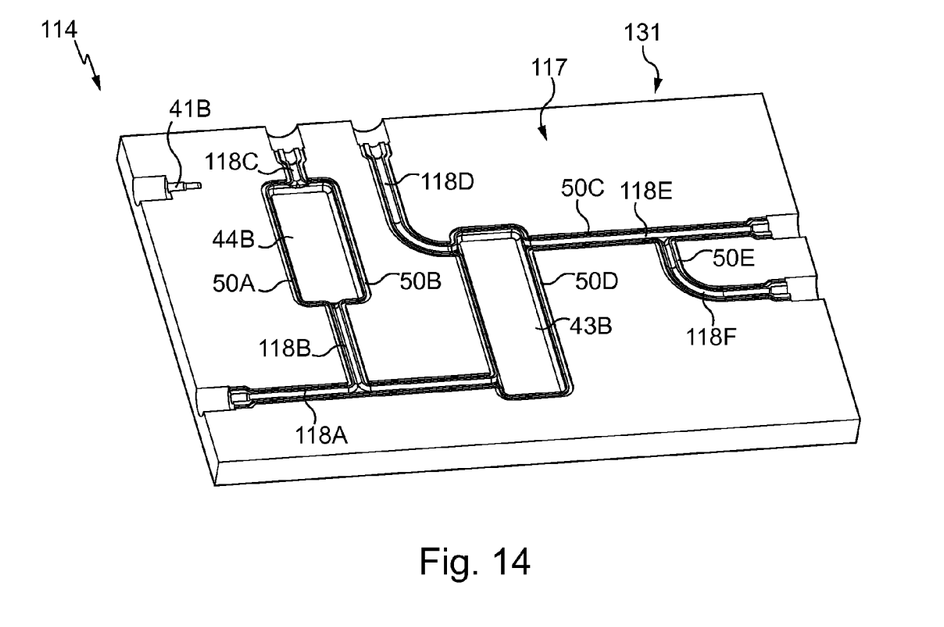
FIGS. 14 to 16 are similar views to FIGS. 10 to 12, but for the upper shell.
Figure 15:
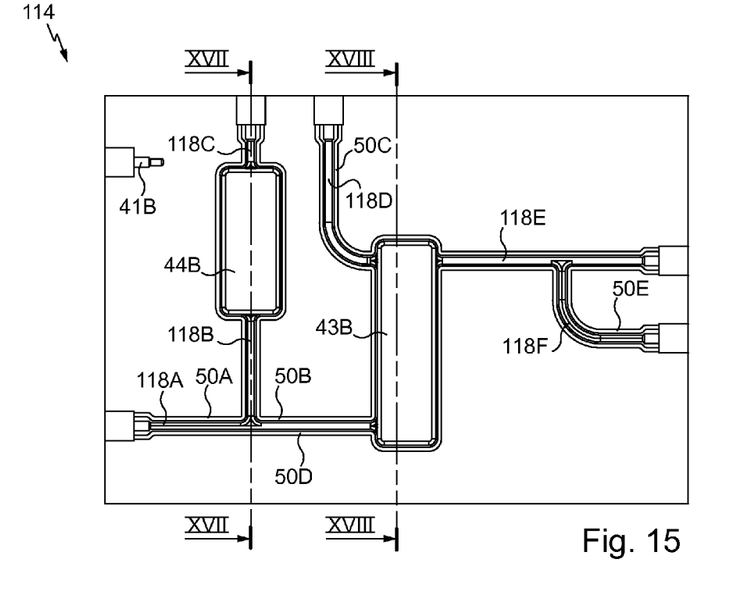
Figure 16:
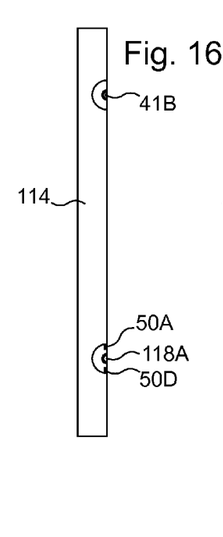
Figure 17:
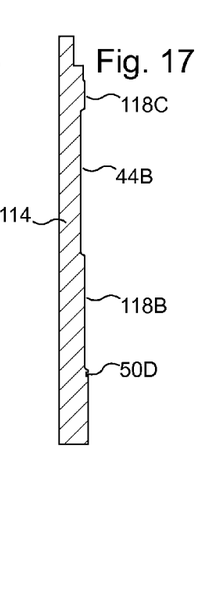
FIGS. 17 and 18 are section views on XVII-XVII and XVIII-XVIII of FIG. 15.
Figures 18, 19:
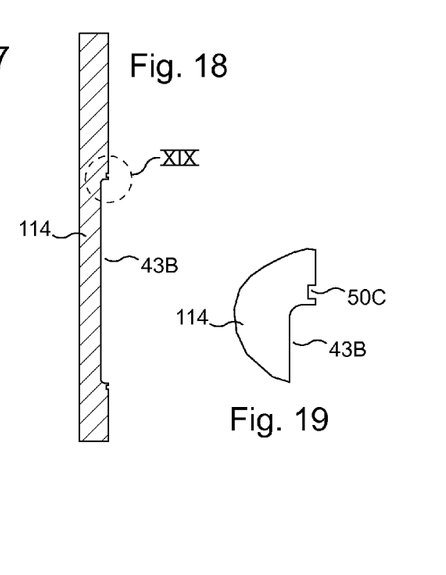
FIG. 19 is an enlargement of the detail identified by XIX in FIG. 18.

To accommodate filters 43 and 44, each of the shells 113 and 114 has a corresponding cavity, respectively 43A, 44A in shell 113 and 43B, 44B in shell 114.

Channels 116A to 116F of shell 113 and channels 118A to 118F of shell 114 are provided to shape pipes 112A to 112F respectively on bag 111.

Each of the channels 116A to 116F and 118A to 118F is capable of accommodating at its corresponding end or ends one of the connectors 40A to 40E or one of the end pieces of the filters 43 and 44.

In order to accommodate connector 41, shells 113 and 114 respectively comprise a cavity 41A and a cavity 41B.

Figure 8:
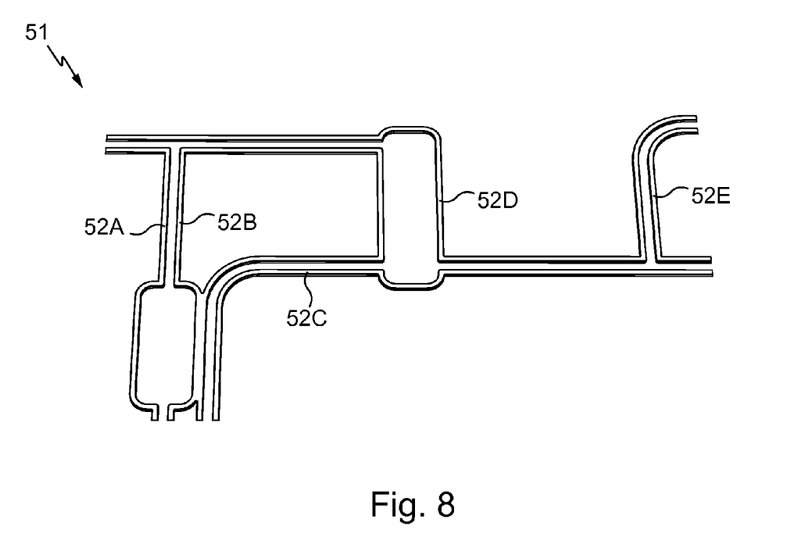
FIG. 8 is a perspective view of a network of beads provided to be placed in grooves of the face of the lower shell of FIG. 4 that is intended to be in contact with the bag.

Each of the channels 116A to 116F as well as each of the cavities 43A and 44A is bordered on each side by a groove 50A to 50E serving to accommodate a respective one of the beads 52A to 52E of the network of beads 51 shown in FIG. 8.

Each of the beads 52A to 52E of network 51 is slightly thicker than the depth of grooves 50A to 50E such that the beads of network 51 each project from the reference surface 115.

Thus, along each of the channels 116A to 116F, 118A to 118F and along the cavities 43A, 44A, 43B and 44B, the films 125 and 126 are pinched between a bead of network 51 and surface 117 of shell 114, when shells 113 and 114 clamp bag 111.

This enables the pipes 112A to 112F to be delimited particularly precisely and to ensure fluid-tightness between films 125 and 126 along those pipes.

As a variant, beads 52A to 52E not only have a pinching function, but also play the role of a heating device (here, electrical resistors) enabling the films 125 and 126 to be welded, in order to make the delimitation of pipes 112A to 112F permanent.

To ensure that shells 113 and 114 are properly positioned relative to each other in the closed state of press 110, shell 113 is provided in each corner with a boss 55, here an outline of right-angled triangle form similar to that of the openings 42 of bag the 111, whereas shell 114 is provided, at the corresponding locations, with cavities 56 of complementary form to that of bosses 55.

To properly position bag 111, the operator takes care to engage the filters 43 and 44 in the cavities 43A and 44A as well as to engage each of the four bosses 55 in the corresponding opening 42 of bag 111.

The shaping of bag 111 by press 110 is carried out as for the shaping of bag 11 by press 10.

Once bag 111 has been clamped between shells 113 and 114, the circuit formed by press 110 and bag 111 is ready to be placed in service.

It will be noted that in FIG. 7 the apertures 57A to 57D can be seen by which the distal end of sensors 121A to 121D can come into contact respectively with pipe 112A (sensors 121A and 121B), pipe 112D (sensor 121C) and pipe 112E (sensor 121D).

Similarly, in FIG. 9 the apertures 58A to 58G can be seen by which the finger of the actuators 120A to 120G can come to respectively pinch pipe 112A (actuators 120A and 120B), pipe 112B (actuator 120C), pipe 112D (actuator 120D), pipe 112E (actuators 120E and 120G), and pipe 112F (actuator 120F).

Figure 6:
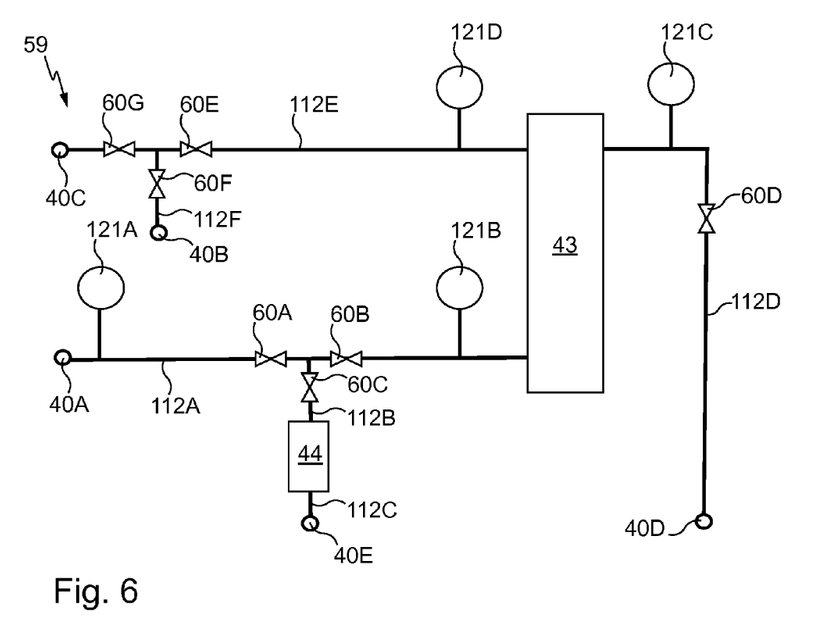
FIG. 6 is a diagram of the circuit which the shells and the bag illustrated in FIGS. 4 and 5 enable to be obtained.

FIG. 6 diagrammatically shows the circuit 59 provided by press 110 and bag 111. On this circuit valves 60A to 60G are respectively formed by the actuator 120A to 120G, by the pipe portion which the finger of that actuator can pinch, and by the portion of shell 113 against which the pipe bears when it is pinched by the finger.

In the illustrated example, the inflation of bag 111 by injection of a pneumatic agent through connector 41 has been made possible by the fact that each of the connectors 40A to 40E was obturated by a plug.

To place circuit 59 in service, these plugs are removed and connectors 40A to 40E are connected to the rest of the installation for treating biological liquid of which circuit 59 is intended to form part.

In circuit 59, filter 43 is here a tangential flow filter (TFF) and filter 44 is a final filter.

Connector 40A is provided to be connected to the delivery side of a feed pump, connector 40B to the delivery side of a transfer pump, connector 40C to a connector of a feed bag of which another connector is connected to the inlet side of the feed pump, connector 40D to the drain, and connector 40E to a bag for collecting treated liquid.

Connector 40B serves to inject the liquid to treat into a loop formed by pipe 112E, by the feed bag connected to connector 40C, by the feed pump of which the inlet side is connected to another connector of the feed bag and of which the delivery side is connected to connector 40A, by pipe 112A and by filter 43.

On injection of the liquid to treat by connector 40B, all the valves are open, except for valves 60E and 60A.

Once the product to treat has been transferred into the feed bag, valves 60F and 60C are closed, whereas the other valves are open and the feed pump is put into operation, such that the liquid to treat flows in the aforementioned loop.

On passage into filter 43, the product to treat is purified with the retentate passing into pipe 112E and the filtrate passing into pipe 112D then being evacuated to the drain.

When the liquid has sufficiently circulated in the loop and has attained the required characteristics of purity and concentration, its evacuation is performed to the collecting bag connected to connector 40E, by passing valve 60B to the closed position and valve 60C to the open position, the treated liquid thus attaining connector 40E by passing via filter 44 where the liquid undergoes a final filtration.

It will be noted that the circuit 59 is capable of implementing, in addition to the operations described above, various other operations by virtue of the routing network formed by pipes 112A to 112F and by virtue of valves 60 to 60G which enable that network to adopt various configurations.

Sensors 121A to 121B are all pressure sensors here. They enable the proper operation of the installation to be verified, and in particular to detect any occurrence of excess pressure (sensor 121A) and to ensure proper operation of filter 43 (sensors 121B to 121D).

FIGS. 10 to 19 illustrate a variant of shells 113 and 114 in which grooves 50A to 50E for the network 51 of beads 52A to 52E is provided on shell 114 rather than on shell 113; whereas the path of channels 116A to 116F (shell 113) and 118A to 118F (shell 114) is arranged slightly differently, in particular in order to minimize the length of pipes 112A and 112E.

In the drawings, shell 13, 13' or 113' is below shell 14 or 114. Consequently, in the present description, the shells are sometimes respectively called lower shell and upper shell. However, there is nothing mandatory about this positioning and on the contrary shells 13, 13', 113 and 14, 114 may be disposed differently, for example with shell 14, 114 below shell 13, 13', 113 or else with the two shells disposed vertically rather than horizontally.

In the examples described above, the bag is inflated before being clamped between the shells. In a variant not illustrated, the bag is first clamped between the shells before being inflated. Of course, in this variant, the films such as 25, 125 and 26, 126 enlarge to conform to the recessed surfaces of the shells. In still another variant not illustrated, the bag is partially inflated before being clamped between the shells and finally inflated after being clamped between the shells.

In variants that are not represented:
the circuit further includes a reservoir able to contain a predetermined volume of liquid, for instance a reservoir included in a loop having a filter with the filtrate evacuated from the loop and the retentate remaining in the loop so as to concentrate the fluid or a buffer reservoir for enabling a physico-chemical value of the liquid such as the Ph to stabilize;
instead of being unitary, the shells are formed by a set of modular members associated together to delimit the different portions of the circuit, with the modular members preferably provided with marks or tags for ensuring that they are correctly arranged relative to one another, the marks or tags being for example written reference numbers or codes and/or wireless means such as RFID tags;
the shells are of a material other than stainless steel, for example of aluminum, plastic, ceramic or wood;
the shaping channels for the pipes comprised by the shells are arranged differently, with, for example channels formed in only one of the shells whereas in the other shell the surface for contact with the bag is entirely planar; and/or the channels are of a cross-section other than semi-circular, for example an oval or U-shaped cross-section;
the complementary devices mounted on the shells are arranged differently, are different from actuators for pinch valves or from sensors of a physico-chemical value such as pressure, Ph or temperature, or are even eliminated;
the films of the bag such as 11 or 111 are of a material other than PureFlex™ film, for example in another film of several layers compatible with biological liquids such as HyQ® CX5-14 film from the company Hyclone industries or Platinum UltraPack film from the company Lonza;
the operation of injecting an inflating agent at higher pressure than atmospheric pressure is replaced by the suction of the faces of the bag such as 11 or 111 by the faces in contact of the shell, the injection of the inflating agent then corresponding to the mere entry of air into the bag which consequently occurs; and/or the injection of the inflating agent is carried out at the same time by suction at the shells and by injection of an inflating agent at higher pressure than atmospheric pressure (of course, suction by the shells is carried out by virtue of the presence thereon of channels opening on the face provided to be in contact with the bag, those channels being linked to a vacuum source);

the inflating agent injected by the connector such as 41 is different from a pneumatic agent, for example water or another liquid inflating agent; and/or there is more than one inflating connector or that connector is eliminated with the inflating agent being injected by one of the routing network connectors;

the pipes of the bag such as 11 or 111, rather than being totally inexistent at the initial state of the bag, are partially preformed; and/or the circuit formed is different from the circuit 59 with, for example, a number of pipes, of connectors and of filters different, for example a single filter, or even no filter, for example to perform a chromatography operation.

Numerous other variants are possible according to circumstances, and in this connection it is to be noted that the invention is not limited to the examples described and shown.

The invention claimed is:

1. A circuit for biological liquid, comprising a plurality of connectors comprising routing network connectors and an inflating connector, and a network for routing liquid between said connectors, a disposable bag comprising two flexible films attached together by a seal delimiting a closed contour with said routing network connectors and inflating connector, said closed contour having an inside and an outside, said routing network connectors and inflating connector each opening respectively inside said closed contour and outside said closed contour; and a press as two shells, said shells each comprising at least one recessed channel, and said press having a first open position during which said two flexible films of said disposable bag abut each other over their lengths and are devoid of pipes, and a second position where said press clamps said disposable bag in a state in which are formed, between said two flexible films of said disposable bag, pipes of said network for routing liquid, inflated by a pneumatic inflating agent injected into said disposable bag clamped between said shells, at least one said pipe having a contour of which at least one portion is delimited exclusively by cooperation with said press, and wherein said shells comprise a surface and a recessed channel recessed with respect to said surface for said at least one pipe having a contour of which at least one portion is delimited exclusively by cooperation with said press, wherein said injecting of said pneumatic inflating agent causes said pipes to each be formed into conformity with opposing recessed channels of the two shells to define said contour of which at least one portion is delimited exclusively by cooperation with said press.

2. A circuit according to claim 1, wherein each said recessed channel is of semi-circular cross-section.

3. A circuit according to claim 1, wherein each said recessed channel is bordered on each side by a groove in which is accommodated a respective bead of a network of beads serving to apply said films against one another along said pipes.

4. A circuit according to claim 1, wherein at least one said shell comprises means for welding said films along said pipes.

5. A circuit according to claim 1, further comprising at least one filter enclosed in said bag.

6. A circuit according to claim 1, wherein at least one said shell comprises at least one actuator of a pinch valve of one of said pipes.

7. A circuit according to claim 1, wherein at least one said shell comprises at least one sensor of a physico-chemical value.

* * * * *